(12) United States Patent
McGowan et al.

(10) Patent No.: US 9,029,607 B2
(45) Date of Patent: May 12, 2015

(54) PROTECTED ALDEHYDES FOR USE AS INTERMEDIATES IN CHEMICAL SYNTHESES, AND PROCESSES FOR THEIR PREPARATION

(75) Inventors: Graham McGowan, Toronto (CA); Boris Gorin, Oakville (CA); Bruce Goodbrand, Hamilton (CA); Elena Bejan, Brantford (CA)

(73) Assignee: Alphora Research Inc., Mississauga (CA)

( * ) Notice: Subject to any disclaimer, the term of this patent is extended or adjusted under 35 U.S.C. 154(b) by 0 days.

(21) Appl. No.: 13/811,305

(22) PCT Filed: Jul. 22, 2011

(86) PCT No.: PCT/CA2011/050451
§ 371 (c)(1),
(2), (4) Date: Mar. 28, 2013

(87) PCT Pub. No.: WO2012/009818
PCT Pub. Date: Jan. 26, 2012

(65) Prior Publication Data
US 2013/0211145 A1    Aug. 15, 2013

(30) Foreign Application Priority Data
Jul. 22, 2010   (CA) ..................... 2710725

(51) Int. Cl.
C07C 45/61    (2006.01)
C07C 45/67    (2006.01)
C07C 45/71    (2006.01)
C07C 47/575   (2006.01)

(52) U.S. Cl.
CPC ............... C07C 45/61 (2013.01); C07C 45/67 (2013.01); C07C 45/71 (2013.01); C07C 47/575 (2013.01)

(58) Field of Classification Search
CPC ............................. C07C 45/67; C07C 45/71
USPC .................................. 568/433, 442
See application file for complete search history.

(56) References Cited

U.S. PATENT DOCUMENTS

| | | | |
|---|---|---|---|
| 4,306,075 A | 12/1981 | Aristoff | |
| 4,486,598 A | 12/1984 | Aristoff | |
| 4,537,346 A | 8/1985 | Duprez | |
| 5,810,071 A | 9/1998 | Pavlin | |
| 5,950,715 A | 9/1999 | Jonsson et al. | |
| 6,182,749 B1 | 2/2001 | Brost et al. | |
| 6,441,245 B1 | 8/2002 | Moriarty et al. | |
| 6,700,025 B2 * | 3/2004 | Moriarty et al. | 568/734 |
| 6,765,117 B2 | 7/2004 | Moriarty et al. | |
| 6,809,223 B2 † | 10/2004 | Moriarty et al. | |
| 7,371,888 B2 * | 5/2008 | Zhao et al. | 560/61 |
| 7,417,070 B2 | 8/2008 | Phares et al. | |
| 2009/0163738 A1 | 6/2009 | Batra et al. | |
| 2011/0319641 A1 | 12/2011 | Batra et al. | |

(Continued)

FOREIGN PATENT DOCUMENTS

| | | |
|---|---|---|
| CA | 1201712 | 3/1986 |
| CA | 2307163 C | 5/1999 |
| CA | 2847985 A1 | 5/1999 |

(Continued)

OTHER PUBLICATIONS

Lukac et al. The Methoxybenzyl Ethers As Useful Protecting Groups for Hydroxy Compounds: Methods of Deprotection. Acta Facultatis Pharmaceuticae Universitatis Comenianae; Tomus LII, 2005, p. 31-32.*

(Continued)

*Primary Examiner* — Sikarl Witherspoon
(74) *Attorney, Agent, or Firm* — Nixon Peabody LLP

(57) ABSTRACT

A para-methoxy protected benzaldehyde useful in preparation of treprostinil, and of formula: (Formula (1)) is prepared by subjecting to Claisen re-arrangement a substituted benzaldehyde of formula (1a): (Formula (Ia)) to form the m-hydroxy-substituted benzaldehyde of formula (1b): (Formula (Ib)) and then reacting compound (1b) with a p-methoxybenzyl (PMB) compound to form a PMB-substituted benzaldehyde of formula (1).

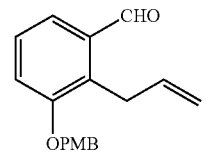

(1)

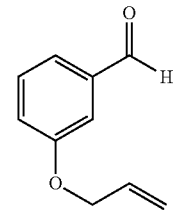

(Ia)

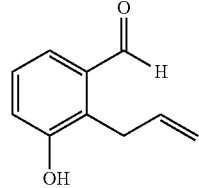

(Ib)

5 Claims, No Drawings

(56) References Cited

U.S. PATENT DOCUMENTS

2012/0190888 A1† 7/2012 Batra et al.
2012/0197041 A1 8/2012 Batra et al.

FOREIGN PATENT DOCUMENTS

| CA | 2698721 A1 | 3/2009 |
| CA | 2777070 | 12/2011 |
| CA | 2710726 | 1/2012 |
| EP | 1611320 B1 | 4/2004 |
| WO | 2004/092552 A2 | 10/2004 |
| WO | 2011153363 | 12/2011 |
| WO | 2012009816 | 1/2012 |
| WO | 2012/088607 | 7/2012 |

OTHER PUBLICATIONS

Danishefsky et al. The Total Synthesis of Quinocarcinol Methyl Ester. Journal of the American Chemical Society, 1985, vol. 107, 1421-1423.*

Li et al. "Synthetic Approaches to the 2002 New Drugs." Mini-Reviews in Medicinal Chemistry, Issue 2, vol. 4, pp. 207-233.

Remodulation Injection Package Insert, Jan. 2010.

U.S. Appl. No. 61/351,115, filed Jun. 3, 2010.

Danishefsky et al., "The Total Synthesis of Quinocarcinol Methyl Ester", J. Am. Chem. Soc., vol. 107, No. 5, pp. 1421-1423, 1985.

Greene et al., "Protective Groups in Organic Synthesis", 3rd ed., John Wiley & Sons, Inc., pp. 86-91, 1999.

Horita et al., "On the Selectivity of Deprotection of Benzyl, MPM (4-Methoxybenzyl) and DMPM (3,4-Dimethoxybenzyl) Protecting Groups for Hydroxy Functions", Tetrahedron, vol. 42, No. 11, pp. 3021-3028, 1986.

Moriarty et al., "The Intramolecular Asymmetric Pauson-Khand Cyclization as a Novel and General Stereoselective Route to Benzindene Prostacyclins: Synthesis of UT-15 (Treprostinil)", J. Org. Chem., vol. 69, Iss. 6, pp. 1890-1902, 2004.

Office Action in U.S. Appl. No. 13/811,301 mailed on Mar. 24, 2014 (151 pp.).

Office Action in U.S. Appl. No. 13/520,872 mailed on Mar. 24, 2014 (32 pp.).

International Preliminary Report on Patentability received in PCT/CA2011/050451 (6 pp.), Dec. 20, 2012.

Written Opinion of the International Searching Authority received in PCT/CA2011/050448 (4 pp.), Sep. 15, 2011.

Greene and Wuts, Protective Groups in Organic Synthesis, Second Edition, John Wiley & Sons, Inc., 1991, pp. 10-142.†

J. Stresinka, "Claisen rearrangement of allyl aryl ethers," Chem. Zvesti, 1976, 30(2):237-245.†

Tsai et al., "A New Synthesis of Benzofurans from Phenols via Claisen Rearrangement and Ring-Closing Metathesis," Journal of the Chinese Chemical Society, 2004, 51:1307-1318.†

* cited by examiner
† cited by third party

PROTECTED ALDEHYDES FOR USE AS INTERMEDIATES IN CHEMICAL SYNTHESES, AND PROCESSES FOR THEIR PREPARATION

FIELD OF THE INVENTION

This invention relates to chemical synthesis of aldehyde compounds, useful as intermediates in preparation of pharmaceutically active prostacyclins. More specifically, it relates to synthesis of a novel, protected aryl aldehyde which can be used in the synthesis of the pharmaceutically active prostacyclin known as treprostinil, using a modified Claisen rearrangement reaction.

BACKGROUND OF THE INVENTION AND PRIOR ART

A Claisen re-arrangement is a highly stereoselective [3,3]-sigmatropic re-arrangement of allyl ethers or allyl aryl ethers, to yield γ, δ-unsaturated carbonyl compounds or α-allyl substituted phenols, respectively. U.S. Pat. Nos. 6,700,025 and 6,809,223 describe the Claisen re-arrangement reactions of substituted allyl aryl ethers such as 3-allylether benzaldehyde 3, to produce 2-allyl-3-hydroxy benzaldehyde, thus:

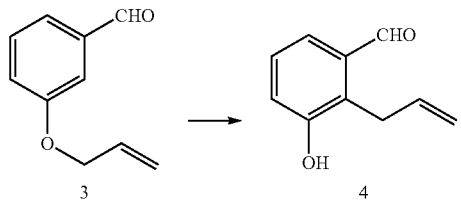

As described in these patents, the reaction is conducted neat, at 150° C. for 41 hours, followed by a series of purifications to yield compound 4.

Aromatic Claisen re-arrangements conducted neat are known to be dangerously reactive, with the potential of producing strong exothermic excursions and high overpressures. Moreover, as the literature often describes, the Claisen re-arrangement applied to allyl aryl ethers generates two isomers, 2-allyl- and 4-allyl, that cannot be separated by various workups and/or column chromatography purifications. Comparable preparations are described in Danishefsky et. al., *J. Am Chem. Soc.*, 1985, 107, 1421-23). This literature reference details a set of conditions for the Claisen rearrangement, 230° C. and N,N-dimethylaniline as solvent, to give a 75:25 mixture of the 2- and 4-allyl isomers, respectively. In this publication, no attempt is described to separate the two isomers until several synthetic steps later. It should also be noted that the solvent mediating this transformation (N,N-dimethylaniline) is toxic, so that it is counter-indicated for use in pharmaceutical synthesis.

These procedures described in the literature, although scalable in a laboratory environment, are not acceptable and safe for the manufacture of protected aldehydes 2,

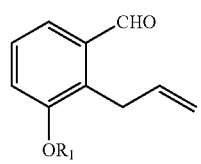

key starting materials in the synthesis of prostacyclins. Furthermore, in several relevant literature references, considerable purification efforts are employed to remove the undesired 4-allyl isomer. Several purification steps such as iterative chromatographies, re-crystallizations and bisulfite adduct formations are required fully to remove this undesired isomer. Accordingly, the conditions available in the literature result into reduced yields and lower process efficiency.

SUMMARY OF THE INVENTION

The present invention provides a novel process for the synthesis of the p-methoxybenzyl (PMB)-protected aldehyde 1:

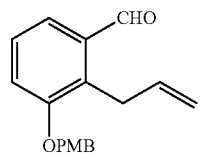

The process of the present invention yields PMB-protected aldehyde 1 is of very high purity, as a result of the choice of conditions used in the synthesis, namely a novel combination of solvent and the selection of the PMB as protecting group. The novel choice of solvents, such as high boiling hydrocarbons and ethers employed in this process allows the isolation of 2-allyl-3-hydroxybenzaldehyde as a solid compound. The PMB-protected aldehyde 1 prepared in this manner is suitable for use in the process of treprostinil synthesis, for example in the treprostinil synthesis described and claimed in our co-pending patent application, serial number NYA, filed on even date herewith under the title "Synthesis of Treprostinil and Intermediates Useful Therein", the disclosure of which is incorporated herein in its entirety. The process of the present invention is robust, efficient and amenable to scale up to industrial levels.

Thus according to a first aspect of the present invention, there is provided a process of preparation of PMB-protected aldehyde 1, of formula:

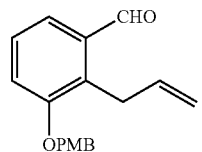

which comprises the following steps:
(a) subjecting the substituted benzaldehyde of formula (Ia); and,

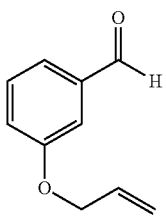

to Claisen re-arrangement to form the m-hydroxy-substituted benzaldehyde of formula (Ib):

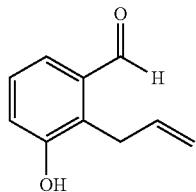

(b) reacting compound (Ib) with p-methoxybenzyl (PMB) reactive compound to form a PMB-substituted benzaldehyde of formula 1

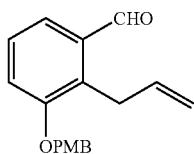

According to another aspect of the invention, there is provided a novel, protected benzaldehyde compound of formula:

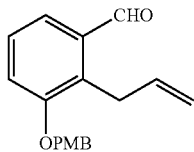

where PMB represents p-methoxybenzyl group.

DESCRIPTION OF THE PREFERRED EMBODIMENTS

A Claisen rearrangement process has been developed that allows the preparation and purification of PMB-protected aldehyde 1, a key starting material for synthesis of treprostinil. The choice of para-methoxybenzyl (PMB) protecting group in addition to being a novel aspect of this invention contributes also to the isolation of the PMB-protected aldehyde 1 as a solid compound. In addition, this novel process utilizes high boiling hydrocarbons or ethers as solvents for the reaction, which allows the reaction to proceed efficiently Furthermore, this novel process utilizes a unique combination of solvents that allows crystallization of 2-allyl-3-hydroxy-benzaldehyde as a white crystalline compound. Compound 1 prepared in this way is substantially free of impurities without the requirement for iterative chromatographies, crystallizations or other purifications. The PMB-protected aldehyde 1 produced by this process is of very high purity and it is suitable for use in the process of treprostinil synthesis.

The preferred process of synthesis of PMB-protected aldehyde 1 according to the invention utilizes the reaction of commercially available 2-hydroxy benzaldehyde with allyl bromide to yield the key intermediate 3. This latter intermediate is then subjected to the Claisen rearrangement to give after isolation and purification compound 4. This aldehyde 4 is then treated with a para-methoxybenzyl compound such as para-methoxybenzyl chloride to yield after isolation and purification a high purity PMB-protected aldehyde 1.

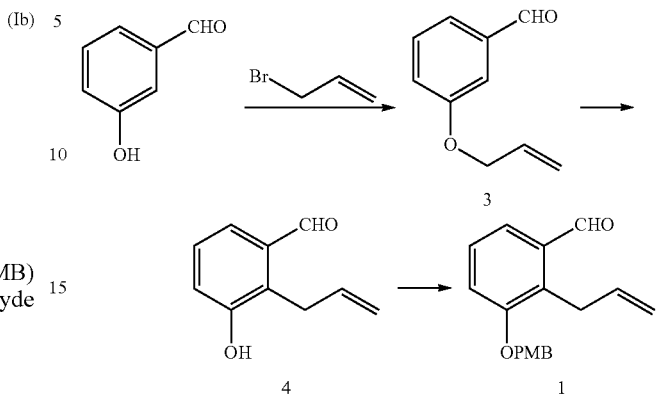

Both compound 1 and compound 4 above are solid, crystalline materials.

The Claisen re-arrangement, conversion of 3 to 4, is conducted in solution in an organic solvent. Appropriate choice of solvent assists in the recovery of the intermediate compounds and/or final compound in pure form, by crystallization. High boiling hydrocarbons or ethers are the solvents for this invention. This choice of solvents according to the invention enables compound 4 to be obtained in high purity. The most preferred solvents for the reaction as well as recrystallization are decalin, xylene, dodecane, toluene and diphenyl biphenyl ether mixtures such as those available under the trade-mark "Dowtherm". Other steps of the process can be conducted in the same or different organic solvents such as ethanol, acetone, etc., choice of which is well within the skill of the art. Conducting the process in solution under reflux conditions is appropriate and preferred for all steps of the preferred process.

Thus a novel process for the synthesis of PMB-protected aldehyde 1 has been described. This novel process provides efficiency over the prior art through the key choices of reaction conditions and protecting group. Moreover, the present invention allows the isolation and purification of PMB-protected aldehyde 1, a key starting material of treprostinil synthesis.

The invention is further illustrated in the following specific, non-limiting Examples.

Example 1

Preparation of 3-Allyloxybenzaldehyde 3

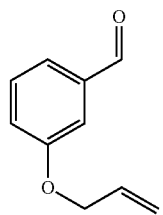

In a 1 L round bottomed flask equipped with mechanical stirrer, reflux condenser and thermometer was added in sequence 400 mL ethanol, 59.63 g of 3-hydroxybenzaldehyde (0.49 moles, 1 eq.), 7.3 g of sodium iodide (48 mmol, 0.1 eq.), 120.98 g of allyl bromide (0.59 moles, 1.2 eq.) and 101.6 g of potassium carbonate (0.74 moles, 1.25 eq.). The reaction mixture was heated to reflux and heating continued for three hours. Heating was then discontinued and the reaction was allowed to cool to room temperature. The mixture was then filtered through a Hyflosupercel pad and ethanol was removed by rotary evaporation. The residual oil was then taken up in 500 mL of MTBE and the organic phase washed sequentially with 10% aqueous sodium hydroxide, water and brine. After drying over sodium sulfate, filtration and rotary evaporation of solvent 79.7 g of a yellow oil of 3-allyloxy-benzaldehyde (quantitative yield) was obtained.

Example 2

Preparation of 2-allyl-3-hydroxy-benzaldehyde 4

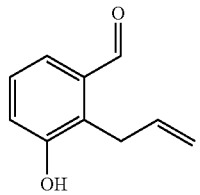

In a 500 ml three-necked Morton flask equipped with mechanical stirrer, thermometer and reflux condenser was added 100 g of 3-allyloxybenzaldehyde (0.62 moles, 1 eq.) and 150 g of cis/trans decalin (1.5 vol). The mixture was purged with nitrogen and then heated to a reflux temperature of 217° C. The reaction was maintained at this reflux temperature for seven hours then cooled and 231 mL of toluene was added. The reaction mixture was then allowed to cool to room temperature. After stirring for 18 hours and further cooling to 0-5° C., reaction mixture was filtered and the cake washed with 200 mL of heptane. The wet cake was stirred in 200 mL of heptane for 1-2 hours at room temperature. After filtration and drying of the cake at 40° C., 54.27 g of crude 2-allyl-3-hydroxybenzaldehyde were obtained. This represents a recovery of 82% of the available 2-allyl product produced by the Claisen rearrangement.

Example 3

Preparation of 2-allyl-3-(4-methoxy-benzyloxy)-benzaldehyde 1

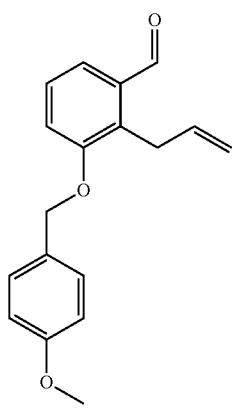 [SMILES: C=CCc1c(C=O)cccc1OCc1ccc(OC)cc1]

In a 1 L three necked round bottom flask equipped with a mechanical stirrer, thermometer and reflux condenser was added 300 mL acetone, 23.19 g of 2-allyl-3-hydroxybenzaldehyde (0.143 mole, 1 eq), 2.13 g of sodium iodide (14 mmol., 0.1 eq), 39.52 g of potassium carbonate (28.6 mmol., 2 eq.) and 22.39 g of p-methoxybenzyl chloride (14.3 mmol., 1 eq.). The reaction mixture was heated to reflux for 4 hours. After cooling to room temperature, the reaction mixture was filtered through a bed of Hyflosupercel and the solvent removed by rotary evaporation. The residual dark oil was taken up in 200 mL of toluene and washed sequentially with 10% aqueous sodium hydroxide, water and brine. The organic phase was dried over sodium sulfate and decolourized with 5 g Darco G60. After filtration through a Celite pad, the solvent was removed by rotary evaporation to give 35.5 g of oil which was then recrystallized from 175 mL of hot IPA. After cooling to room temperature and further cooling to 0-5° C., the solids were filtered and washed with IPA to afford after drying at 40° C., 24.74 g (61%) of 2-allyl-3-(4-methoxy-benzyloxy)-benzaldehyde as an off-white solid.

What is claimed is:
1. A process of preparation of PMB-protected aldehyde 1, of formula:

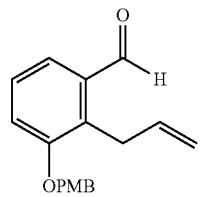

1 which comprises:
(a) subjecting to Claisen re-arrangement a substituted benzaldehyde of formula (1a):

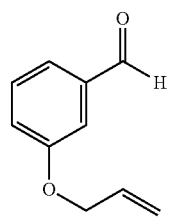

1a to form the m-hydroxy-substituted benzaldehyde of formula (1b); and,

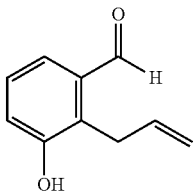

1b (b) reacting compound (1b) with a p-methoxybenzyl halide compound to form a PMB-substituted benzaldehyde of formula 1

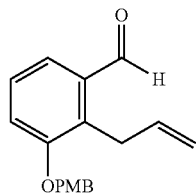

wherein Step a) is performed in an organic solvent, and the organic solvent is an inert, high boiling hydrocarbon or ether, or a mixture thereof.

2. The process of claim 1 wherein the oxyalkene-substituted benzaldehyde of formula (1a) is prepared by reaction of the m-hydroxybenzaldehyde with an allyl halide.

3. The process of claim 2 wherein the organic solvent is decalin.

4. The process of claim 2 wherein the organic solvent is decalin, toluene mixture.

5. A compound of formula 1:

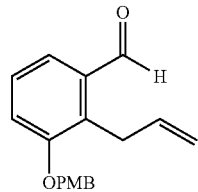

where PMB represents p-methoxybenzyl protecting group.

* * * * *